United States Patent [19]
Figueroa et al.

[11] Patent Number: 5,873,879
[45] Date of Patent: Feb. 23, 1999

[54] DEVICE FOR INSERTING A FLEXIBLE INTRAOCULAR LENS

[75] Inventors: Dennis Alexander Figueroa, Mission Viejo; Alok Nigam, Trabuco Cyn; Thomas Michael Heyman, Poway, all of Calif.

[73] Assignee: Chiron Vision Corporation, Claremont, Calif.

[21] Appl. No.: 961,231

[22] Filed: Oct. 30, 1997

Related U.S. Application Data

[63] Continuation of Ser. No. 286,557, Aug. 5, 1994, abandoned.

[51] Int. Cl.⁶ .................................................. A61B 17/00
[52] U.S. Cl. ............................................. 606/107; 623/6
[58] Field of Search ................................... 606/107, 108, 606/161, 167; 623/6

[56] References Cited

U.S. PATENT DOCUMENTS

| | | |
|---|---|---|
| 3,991,426 | 11/1976 | Flom et al. . |
| 4,053,953 | 10/1977 | Flom et al. . |
| 4,214,585 | 7/1980 | Bailey, Jr. . |
| 4,244,370 | 1/1981 | Furlow et al. . |
| 4,573,998 | 3/1986 | Mazzocco . |
| 4,681,102 | 7/1987 | Bartell ....................................... 606/107 |
| 4,699,140 | 10/1987 | Holmes et al. . |
| 4,702,244 | 10/1987 | Mazzocco . |
| 4,715,373 | 12/1987 | Mazzocco et al. . |
| 4,747,404 | 5/1988 | Jampel et al. . |
| 4,763,650 | 8/1988 | Hauser . |
| 4,765,329 | 8/1988 | Cumming et al. . |
| 4,822,360 | 4/1989 | Deacon . |
| 4,834,094 | 5/1989 | Patton et al. . |
| 4,836,201 | 6/1989 | Patton et al. . |
| 4,836,202 | 6/1989 | Krasner . |
| 4,880,000 | 11/1989 | Holmes et al. . |
| 4,919,130 | 4/1990 | Stoy et al. . |
| 4,934,363 | 6/1990 | Smith et al. . |
| 4,955,889 | 9/1990 | Van Gent . |
| 4,957,505 | 9/1990 | McDonald . |
| 4,976,716 | 12/1990 | Cumming ................................. 606/107 |
| 5,007,913 | 4/1991 | Dulebohn et al. . |
| 5,098,439 | 3/1992 | Hill et al. . |
| 5,123,905 | 6/1992 | Kelman . |
| 5,190,552 | 3/1993 | Kelman . |
| 5,242,450 | 9/1993 | McDonald . |
| 5,275,604 | 1/1994 | Rheinish et al. ......................... 606/107 |
| 5,304,182 | 4/1994 | Rheinish et al. . |
| 5,395,378 | 3/1995 | McDonald ............................... 606/107 |
| 5,494,484 | 2/1996 | Feingold . |
| 5,496,328 | 3/1996 | Nakajima et al. . |
| 5,499,987 | 3/1996 | Feingold . |

Primary Examiner—Robert A. Hafer
Assistant Examiner—Benjamin K. Koo
Attorney, Agent, or Firm—Banner & Witcoff, Ltd.

[57] ABSTRACT

A device for inserting a flexible intraocular lens into an eye comprising a tubular member and a plunger. The tubular member includes a staging area, a lumen and an open distal end. The staging area supports the lens in an unstressed state prior to engagement by the plunger. In the unstressed state, the optic of the lens is suspended in a pocket to avoid any substantial contact with interior portions of the tubular member. The plunger includes a slot in its distal tip for receiving and gripping the lens. With this construction, the lens can be inserted into the eye in one continuous motion. Further, the plunger holds the lens when the lens is moved out of the tubular member.

7 Claims, 9 Drawing Sheets

DEVICE FOR INSERTING A FLEXIBLE INTRAOCULAR LENS

This is a continuation of application Ser. No. 08/286,557, filed on Aug. 5, 1994 abandoned.

FIELD OF THE INVENTION

The present invention pertains to a device for inserting a flexible intraocular lens (IOL) into the eye of a patient.

BACKGROUND OF THE INVENTION

The natural crystalline lens of the eye plays a primary role in focusing light onto the retina for proper vision. However, the lens can become damaged due to injury or become cloudy because of the aging process or disease and form a cataract. To restore vision to the eye, the natural lens must be surgically removed and an artificial lens implanted as a replacement.

Many surgical procedures have been developed for removing the natural lens. As an example, phacoemulsification is one such process which has gained wide popularity. According to this procedure, a slender implement is inserted through an incision made in the eye and into the natural lens. The implement produces ultrasonic vibrations and emulsifies the lens. The emulsified portions of the lens are then aspirated out of the eye through a passage provided in the implement. As opposed to other procedures, this lens extraction method requires the surgeon to make only a narrow incision in the eye. In general, the use of a small incision can lessen the trauma and complications experienced during the surgery and postoperatively.

A flexible IOL comprises a central optic portion which focuses light on the retina and at least one outwardly extending haptic. Haptics can have a variety of different configurations, but most commonly are either a plate-like extension of the optic or loop shaped. In any event, the haptics extend outwardly to position the optic of the lens in alignment with the pupil. Flexible IOLs are particularly suited for insertion in the eye following a phacoemulsification lens extraction procedure. Whereas placement of a hard, non-foldable IOL would require widening of the small phacoemulsification incision, a flexible IOL can be compressed or folded for passage through the narrow incision in the eye. Once the lens is passed through the incision and released into the eye, it will expand to its original shape and size.

A number of different devices have been developed to implant a flexible IOL into an eye. See, for example, U.S. Pat. Nos. 4,573,998 to Mazzocco, 4,681,102 to Bartell, 4,919,130 to Stoy et al., and 5,275,604 to Rheinish et al. In general, these devices function to pass a compressed lens through the narrow incision made in the eye. These devices, however, require undue manipulation of the lens, include a multiplicity of parts, and/or fail to provide ample control of the lens as it enters the eye.

SUMMARY OF THE INVENTION

The present invention is a device which enables flexible IOLs to be easily folded, compressed and inserted through an incision in the eye. In general, the insertion device comprises a tubular member for receiving the lens and a plunger for pushing the lens through the tubular member and into the eye. As the lens is pushed through the passage it is compressed into a smaller configuration. The construction of the present invention ensures an easy, sure and consistent compression of the lens.

According to one aspect of the invention, the tubular member includes a staging area for holding the lens in an unstressed condition. The lens is preferably held in a suspended position by its haptics so that the optic remains substantially free of contact with the interior of the tubular member. In this manner, the device can be used as the lens package, and the device can be shipped and stored with the lens already in place and ready for use. As a result, unnecessary manipulation of the lens is avoided. According to another aspect of the invention, the plunger is provided with walls which hold the lens to the plunger when the lens is pushed out of the tubular member. The distal tip of the plunger is preferably bifurcated to define a slot for partially receiving and gripping the lens. With this construction, the plunger is able to hold the lens when the lens exits the tubular member and expands into the eye. Holding the lens in this manner eases placement of the lens in the eye and alleviates the risks associated with uncontrolled expansion of a lens in the eye.

DETAILED DESCRIPTION OF THE PREFERRED EMBODIMENT

Figure 1:
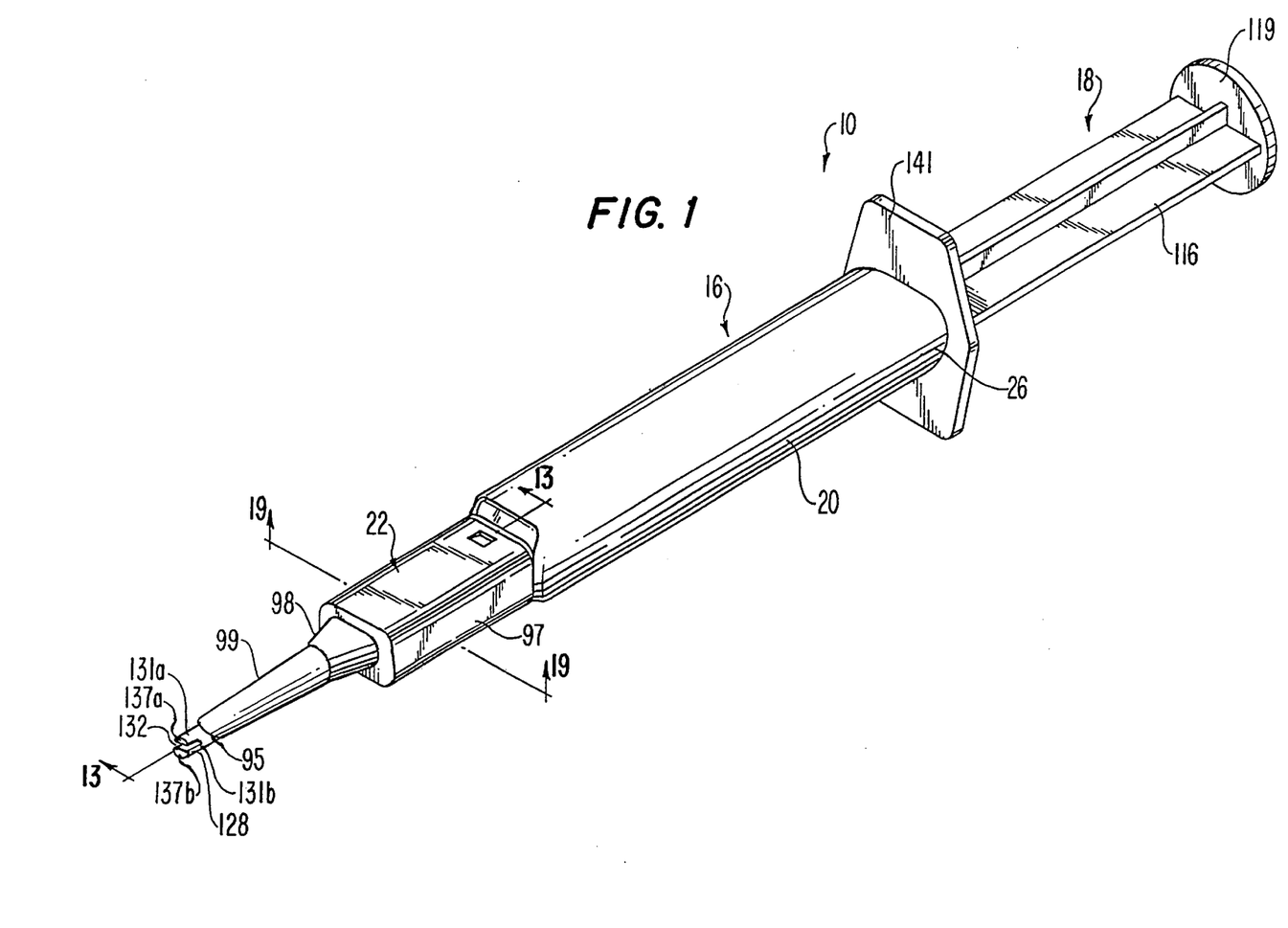
FIG. 1 is a perspective view of an insertion device in accordance with a preferred embodiment of the present invention.
Figure 13:
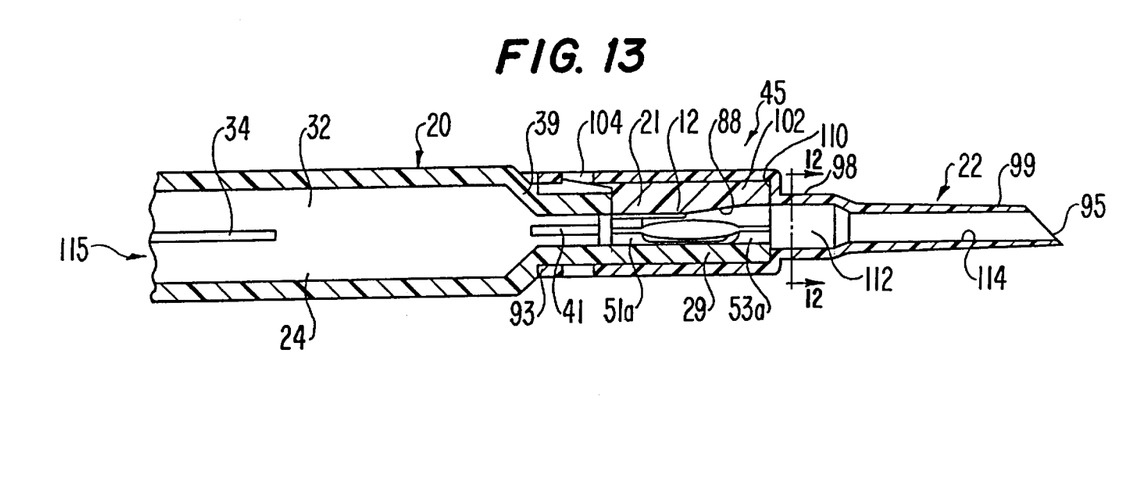
FIG. 13 is a partial cross sectional view taken along line 13—13 in FIG. 1, with an IOL in the staging area.
Figure 14:
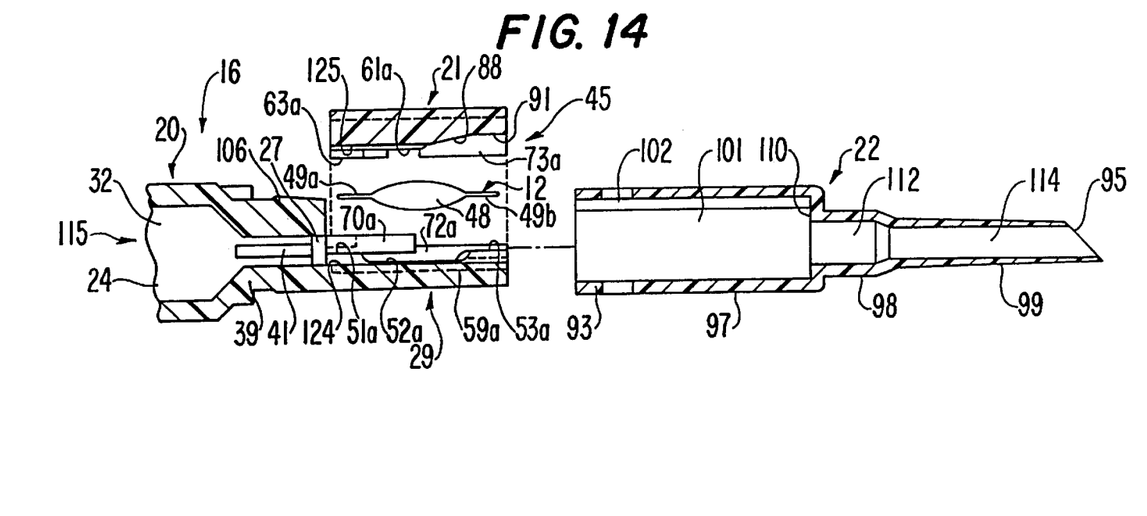
FIG. 14 is an exploded view of FIG. 13.
Figure 15:
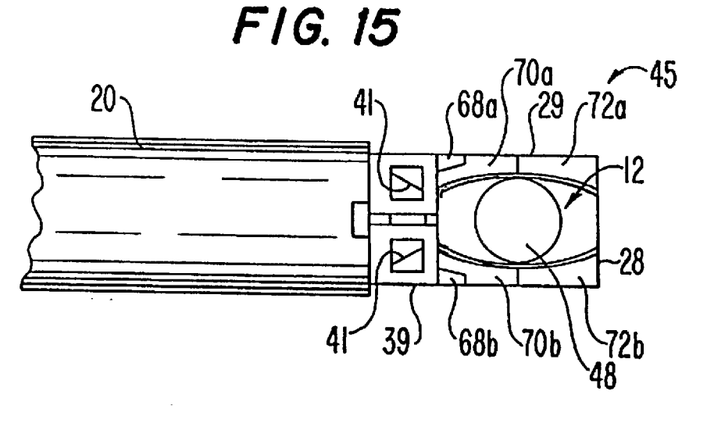
FIG. 15 is a partial top plan view of the tubular unit of the insertion device with an IOL in the staging area and with the cover and cannula omitted.
Figure 16:
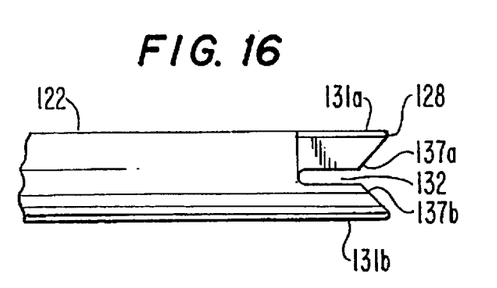
FIG. 16 is side elevational view of the distal tip of the plunger.
Figure 17:
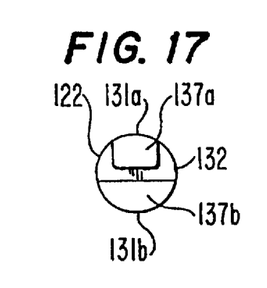
FIG. 17 is a front view of the distal end of the plunger.
Figure 18:
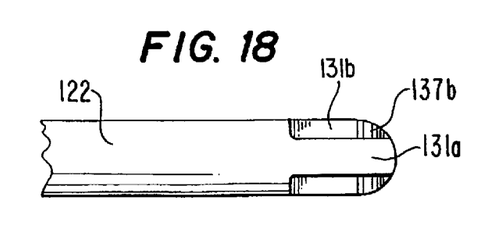
FIG. 18 is a top plan view of the distal end of the plunger.
Figure 26:
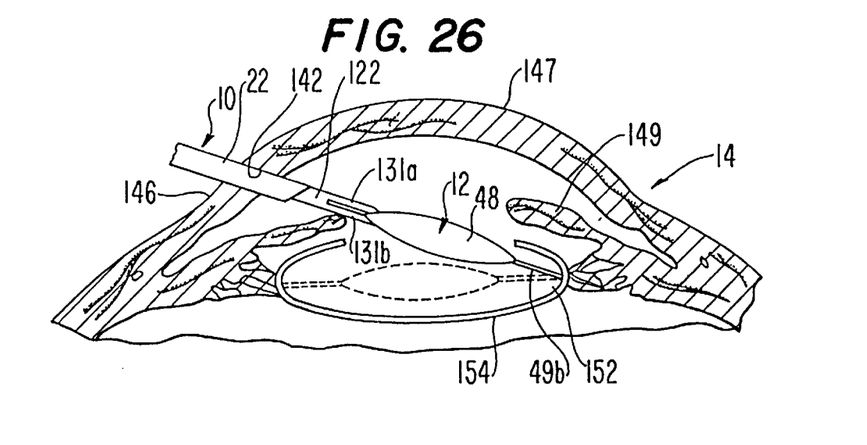
FIG. 26 is a cross sectional view of an eye illustrating the insertion and placement of an IOL.

The present invention pertains to a device 10 (FIG. 1) for inserting a flexible IOL 12 into an eye 14 of a patient (FIG. 26). The device comprises an outer tubular unit 16 and an inner plunger 18. Tubular unit 16 is preferably formed by a base member 20, a cover 21 and a cannula 22 which are coupled together (FIGS. 1, 13 and 14). The components of device 10 may be composed of a plastic or metal material. In the preferred embodiment, the base member 20 and cover 21 are formed of polycarbonate or polypropylene. The plunger 18 and cannula 22 are preferably made of polypropylene. Nevertheless, a wide array of materials could be used.

Figure 5:
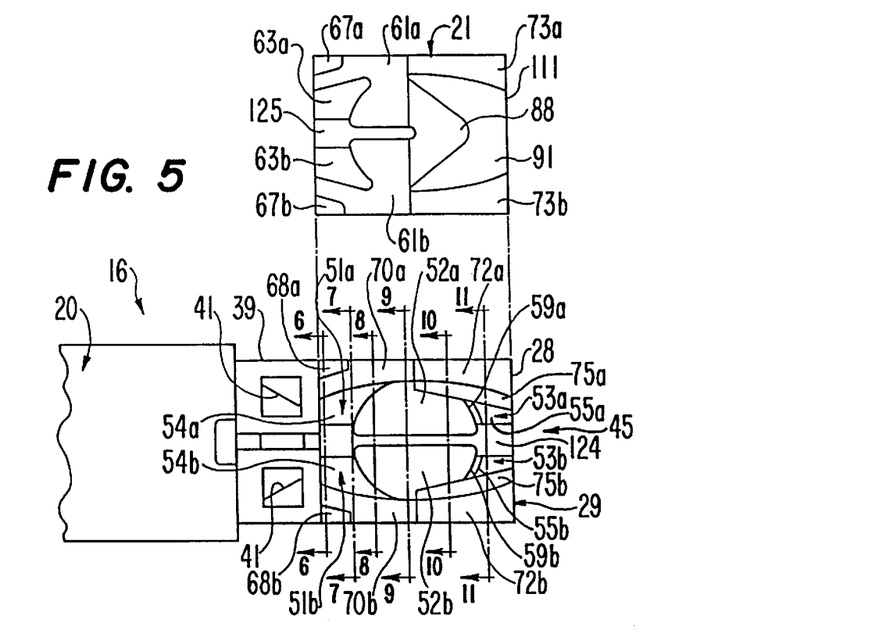
FIG. 5 is a partial top plan view of the tubular unit of the insertion device, including the staging area, with the cover removed and overturned, and the cannula omitted.
Figure 6:
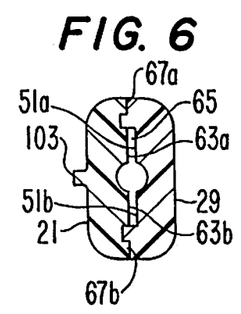
FIG. 6 is a cross sectional view taken along line 6—6 in FIG. 5 with the cover placed onto the shelf segment.
Figure 7:
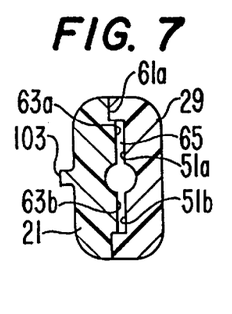
FIG. 7 is a cross sectional view taken along line 7—7 in FIG. 5 with the cover placed onto the shelf segment.
Figure 8:
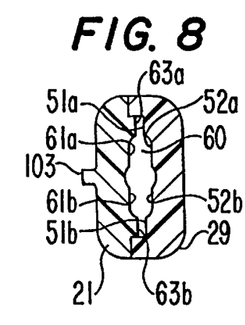
FIG. 8 is a cross sectional view taken along line 8—8 in FIG. 5 with the cover placed onto the shelf segment.
Figure 9:
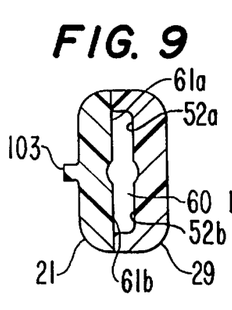
FIG. 9 is a cross sectional view taken along line 9—9 in FIG. 5 with the cover placed onto the shelf segment.
Figure 10:
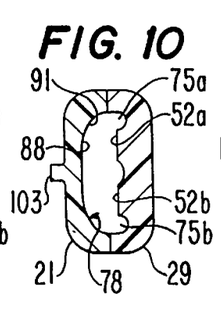
FIG. 10 is a cross sectional view taken along line 10—10 in FIG. 5 with the cover placed onto the shelf segment.
Figure 11:
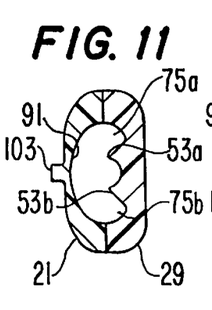
FIG. 11 is a cross sectional view taken along line 11—11 in FIG. 5 with the cover placed onto the shelf segment.
Figure 12:
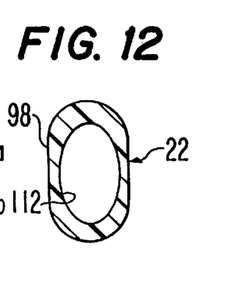
FIG. 12 is a cross sectional view taken along line 12—12 in FIG. 13.

Base member 20 is an elongate tubular member defining an inner passage 24 which is provided with a relatively large opening at proximal end 26 and an opening 27 of reduced size near, but spaced from, distal end 28 (FIGS. 1, 5, 13 and 14). A forwardly extending shelf segment 29 projects beyond opening 27 (FIGS. 5, 13 and 14). Base member 20 preferably has a generally oval cross sectional configuration, although other shapes could be used.

The inner passage 24 of base member 20 is adapted to movably receive therein plunger 18. A longitudinal groove 34 is preferentially positioned along one of the side walls 32 defining inner passage 24 (FIG. 13). Groove 34 cooperates with an extending flange 35 projecting laterally from plunger 18 to ensure that the plunger is properly oriented when fed into base member 20. Nevertheless, the groove construction could be replaced with a different structure for ensuring proper placement, Such as forming at least a portion of inner passage 24 and plunger 18 with a D-shaped configuration. Near distal end 28, base member 20 forms a narrowed neck 39. Neck 39 defines distal opening 27 through which a portion of the plunger is passed to engage lens 12. Converging guideways 41 are positioned along opposite interior sides of passage 24 leading up to neck 39 (FIGS. 5, 13 and 14). Guideways 41 function to ease the passage of the plunger through neck 39 and over the shelf segment 29 for engagement with lens 12.

Figure 24:
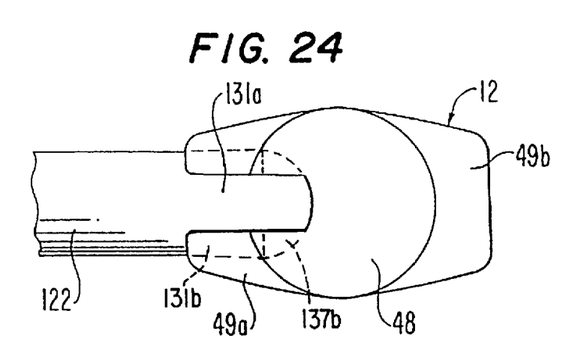
FIG. 24 is an enlarged top plan view of the distal tip of the plunger holding an IOL.

Shelf segment 29 is formed as an extension of roughly one half of the tubular base member 20. Shelf segment 29 cooperates with cover 21 to define a staging area compartment 45 for holding lens 12 (FIGS. 5–11 and 13–14). Lens 12 preferably has a central optic and a pair of adjacent web or plate haptics 49a, 49b (FIGS. 14 and 24). Nevertheless, other lens constructions, such as a lens with loop liaptics, could also be used. The interior side of shelf segment 29 is formed in part by a pair of ledges 51a, 51b adjacent neck 39, a pair of recessed central flats 52a, 52b, and a pair of ramps 53a, 53b spaced forwardly of flats 52a, 52b (FIGS. 5–11 and 13–14). Ledges 51a, 51b and ramps 53a, 53b are each formed with top surfaces 54a, 54b, 55a, 55b to engage and support the haptics 49a, 49b of lens 12 in an initial unstressed position. Ramps 53a, 53b further include sloped surfaces 59a, 59b inclined to flats 52a, 52b. Flats 52a, 52b are recessed relative to top surfaces 54a, 54b, 55a, 55b to define a pocket 60 into which is received optic 48.

Cover 21 lies against shelf segment 29 to form staging area compartment 45 and enclose lens 12 in its initial unstressed position (FIG. 13). Cover 21 includes on its interior side recessed sections 61a, 61bthe central portions of which lie opposed to the proximal half of flats 52a, 52b. A pair of adjacent plateau segments 63a, 63b lie opposed to ledges 51a, 51b to define a gap 65 adapted to matingly receive and hold the proximal haptic 49a. Haptic 49a is loosely received in gap 65 so that it can be easily pushed out of staging area 45 during the insertion process. Ledges 51a, 51bplateau segments 63a, 63b, and ramps 53a, 53b collectively support lens 12 by haptics 49a, 49b. In this initial position, optic 48 is held in suspension in pocket 60 so that the optic avoids contact with the interior walls of the staging area compartment 45.

The lens 12 can be installed in compartment 45 at a manufacturing plant and shipped to the user in device 10 with or without cannula 22 assembled in place. In this manner, device 10 can conveniently serve also as a lens package. Since lens 12 is supported in a generally suspended and unstressed state, the lens can be stored for a substantial length of time, perhaps as long as 10 years. Although the cover could be fixed to base member 20, it is designed for removal to enable inspection of the lens prior to its implantation in the eye. In one embodiment, cover 21 is completely separable from base member 20. However, in the preferred construction, the cover is hinged or otherwise connected to shelf segment 29 or neck 39.

Cover 21 includes projections 67a, 67b which mate with depressions 68a, 68b formed in shelf segment 29. In addition, shelf segment 29 includes proximal outer walls 70a, 70b and distal outer walls 72a, 72b. Proximal walls 70a, 70b abut the outer portions of recessed sections 61a, 61b. Distal walls 72a, 72b likewise abut walls 73a, 73b of cover 21. Distal walls 72a, 72b are preferably recessed relative to proximal walls 70a, 70b to enhance the mating fit of cover 21. During shipping of the device, the cover may be held closed by cannula 22, tape and/or other means to avoid inadvertent release of the lens.

Troughs 75a, 75b are formed in shelf segment 29 by extending the inner side wall surface 78 of compartment 45 downwardly between the outer distal sides of flats 52a, 52b and distal walls 72a, 72b. are provided to receive the opposite sides of lens 12 as they are folded or curled along inner side wall surface 78. In the preferred embodiment, the troughs are deeper than flats 52a, 52b.

Cover 21 further includes a central, generally planar surface 88 inclined to extend away from shelf segment 29. A conically shaped portion 91 generally surrounding inclined surface 88 lies opposed to ramps 53a, 53b. These surfaces 88, 91 in cooperation with ramps 53a, 53b initiate the desired folding of the lens to its compressed state.

Cannula 22 is an elongate tubular member with an open proximal end 93 and an opposite open distal end 95 (FIGS. 1 and 12–14). Cannula 22 is preferably subdivided into three graduated sections 97–99. The proximal section 97 has a generally rectangular configuration and defines an inner cavity 101 sized to matingly receive the assembled shelf segment 29 and cover 21. Section 97 extends from distal end 28 to neck 39 of base member 20 and functions to hold cover 21 against shelf segment 29. An axial channel 102 is defined along one wall of cavity 101 to matingly receive ridge 103 extending up from cover 21. A hole 104 defined at the proximal end 93 of cannula 22 cooperates with a biased lock 106 on base member 20 to secure the cannula in place.

The medial section 98 of cannula 22 is significantly smaller than proximal section 97 so that a rim 110 is defined therebetween. Rim 110 acts as a shoulder in abutment with the aligned distal ends 28, 111 of base member 20 and cover 21. The inner wall of medial section 98 converges to define a funnel shaped passage 112. The funnel portion 112 preferably has an oval cross section, although other shapes could be used. This funnel section causes the lens to become substantially curled and compressed for entry into the eye.

The final, distal section 99 of cannula 22 is a long, narrow tube which defines an inner lumen 114. Distal section 99 is to be inserted through the narrow incision made in the eye. As with medial section 98, distal section 99 and lumen 114 preferably have an oval cross sectional shape. Of course, other shapes could be utilized if desired. To facilitate manufacturing and further compression of lens 12, lumen 114 is formed to taper slightly as it extends forward. Distal end 95 of cannula 22 is beveled to ease the insertion of the cannula into the incision and to assist in facilitating a gradual expansion of the lens as it exits from lumen 114.

Figure 27:
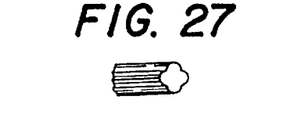
FIG. 27 is a perspective view of an alternative construction of the distal end of the cannula.
Figure 28:
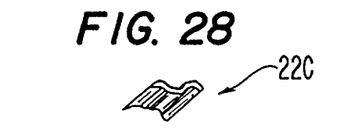
FIG. 28 is a perspective view of a second alternative construction of the distal end of the cannula.
Figure 29:
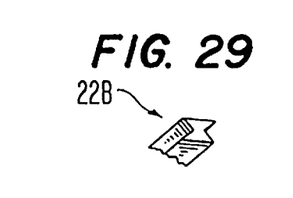
FIG. 29 is a perspective view of a third alternative construction of the distal end of the cannula.
Figure 30:
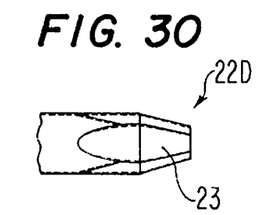
FIG. 30 is a side elevational view of a fourth alternative construction of the distal end of the cannula.
Figure 31:
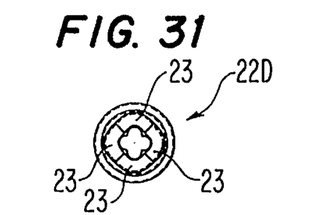
FIG. 31 is a front elevational view of the fourth alternative construction of the distal end of the cannula.

The distal section of the cannula may be provided with a wide variety of cross section configurations. As examples only, the cannula may be shaped with a clover-type tip 22A, a collapsible bag type tip 22B, or a wave-type tip 22C (FIGS. 27–29). These configured tips enhance the strength of the tip and thus permit a narrower construction to be used. The cannula tip may also be formed with a collet-like construction 22D. In this embodiment, the tip includes four separable leaves 23 which are expanded as the lens is pushed into the eye. The leaves 23 are biased to naturally close after the lens is placed into the eye and the plunger retracted.

Figure 2:
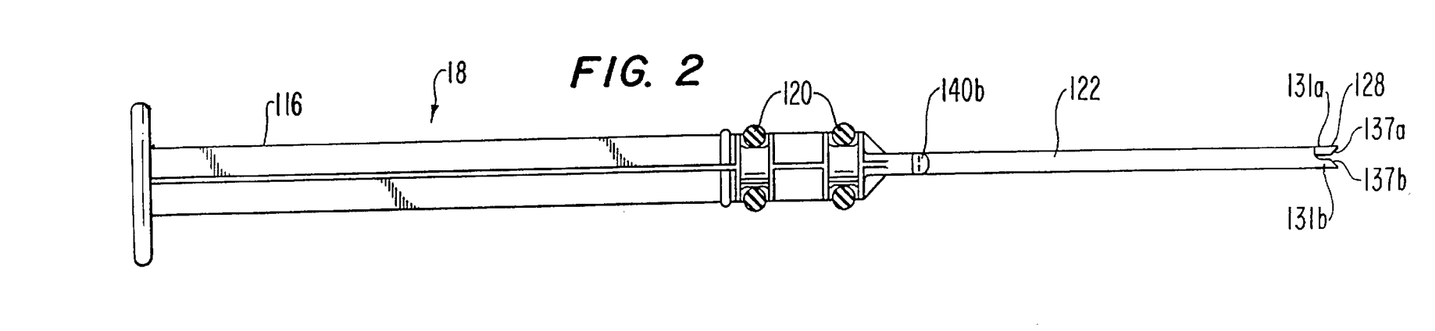
FIG. 2 is a side elevational view of the plunger of the insertion device.
Figure 3:
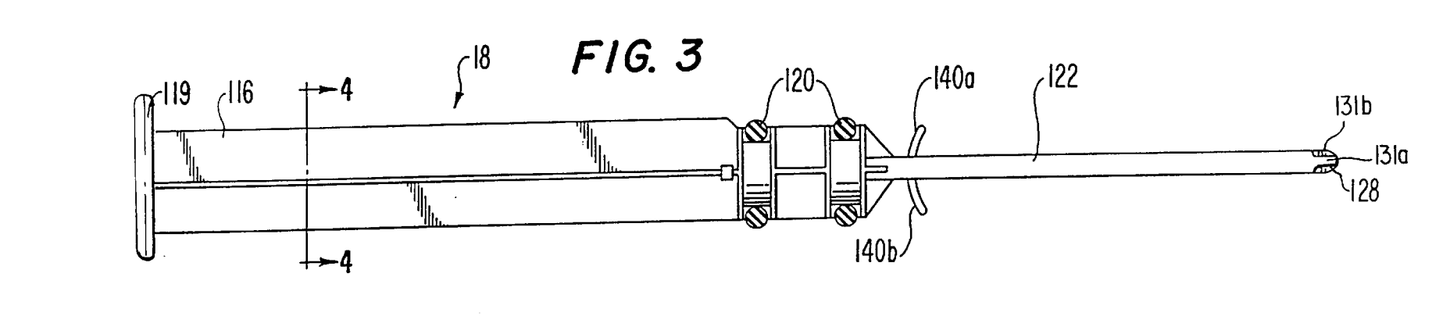
FIG. 3 is a top plan view of the plunger.
Figure 4:
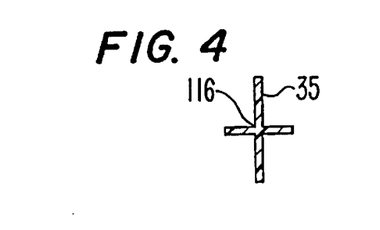
FIG. 4 is a cross sectional view taken along line 4—4 in FIG. 3.

Plunger 18 is an elongate member which is adapted to move through the inner passage 115 defined by tubular unit 16 (FIGS. 1 and 13). The plunger comprises a main body 116 preferably shaped with a cross shaped cross section (FIGS. 2–3). As discussed above, one flange 35 of the body is received into groove 34 to ensure proper placement of the plunger. A flat thumb pad 119 is provided on the proximal end of body 116 for manual operation of the device. Other constructions, however, may be provided to effect advancement of plunger 18 through tubular unit 16. The forward end of body 116 includes a pair of spaced apart O-rings 120a, 120b. The O-rings provide a level of resistance to enable a more controlled manual operation of the plunger. The O-rings further help to prevent the plunger from inadvertent movement when the surgeon manipulates device 10 during the surgical procedure.

Figures 21, 25:
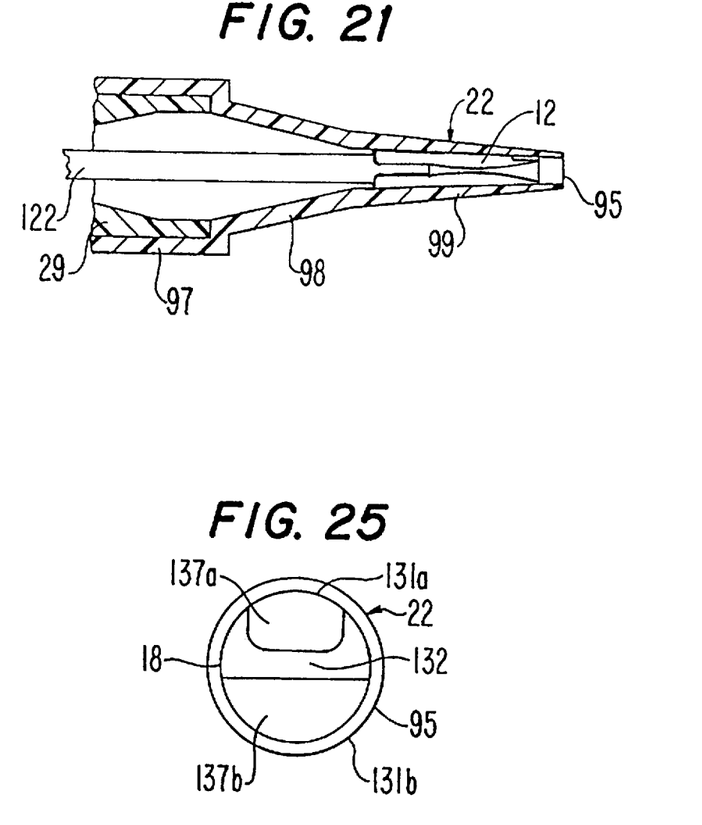
FIG. 25 is a front end view of the insertion device with the plunger extended to the distal end of the cannula.

A slender rod 122 projects forwardly beyond the main body 116 of plunger 18. The rod is intended to pass through staging area 45, funnel 112 and lumen 114. In order to provide sufficient clearance for rod 122, shelf segment 29 defines a channel 124 and cover 21 includes a relief 125 (FIGS. 5–11 and 13–14). Relief 125 only extends partway across cover 21 because surface 88 diverges away from the interior side of shelf segment 29 and thus provides sufficient clearance for rod 122. While rod 122 could have a wide range of shapes, it preferably has a circular shape adapted to pass through the distal end 95 of cannula 22 (FIG. 25).

The distal tip 128 of rod 122 is preferably bifurcated to define a pair of prongs 131a, 131b separated by a slot 132 (FIGS. 2–3, 16–18, 24 and 25). The slot is shaped to receive and hold proximal haptic 49a and optic 48 of lens 12. The ends 135a, 135b of prongs 131a, 131b are chamfered to form a pair of walls 137a, 137b which collectively form a generally V-shaped configuration. Depending on the sturdiness of the proximal haptic, walls 137a, 137b may or may not engage the proximal end of the optic 48. One prong 131a is made narrower than the other prong 131b to allow space for the lens 12 to curl and compress during its passage through lumen 114 and into the patient's eye.

The distal tip of plunger 18 may alternatively be formed with other structural configurations which would hold the lens when the lens is pushed out of the cannula. For example, when implanting an IOL with loop shaped haptics, the plunger may be formed with a closed vertical slot (not shown) along the top of rod 122 in lieu of the open horizontal slot 132. In this arrangement, the lens would be positioned in staging area 45 with the haptics extending from points along the sides of the tubular unit. The haptic, which curls rearwardly would be inserted into the vertical slot when the lens is mounted in the staging area. To avoid inadvertent release of the haptic during shipping and storage, the plunger could be secured in a fixed position through the use of a latch, tape, or other securing means. In any event, the plunger would engage the optic portion of the lens with its distal tip, formed for example with only inclined surfaces like 137a, 137b. When the lens is initially extended beyond cannula 22, the noted haptic would remain entrapped in the slot which would not yet be exposed outside of cannula 22. When release of the lens is desired, the plunger can be pushed slightly farther to expose the vertical slot and free the trapped haptic. The plunger can then be retracted into the tubular unit 16 while the lens remains in the eye.

In one embodiment, a pair of resilient spring elements 140a, 140b extends laterally from rod 122 near the rod's proximal end (FIGS. 2–3). The spring elements function to press against guideways 41 when the free end 128 of rod 122 extends beyond cannula 22. This engagement with guideways 41 forces spring elements 140a, 140b to be pushed backward, and thereby create a biasing force to pull the plunger rearward into tubular unit 16. In the preferred construction, the spring elements (not shown) would extend forwardly, generally parallel with rod 122, from the front end of the main body. In this arrangement, the spring elements would be designed to curl inward upon engagement with guideways 141. Additionally, a coil spring (not shown) may be secured around the plunger/rod to provide the desired biasing force. Of course, other spring arrangements could also be used. The spring may also be omitted and the plunger retracted manually by the surgeon.

Figure 19:
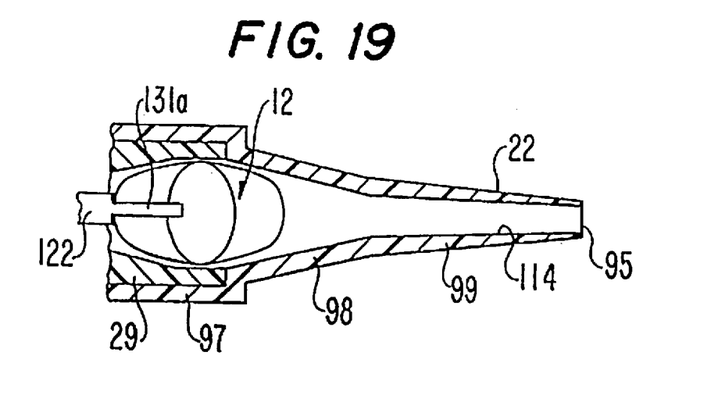
FIGS. 19–23 are each a schematic, partial cross sectional views taken along line 19—19 in FIG. 1, illustrating the movement of the plunger during insertion of the IOL into an eye.
Figure 20:
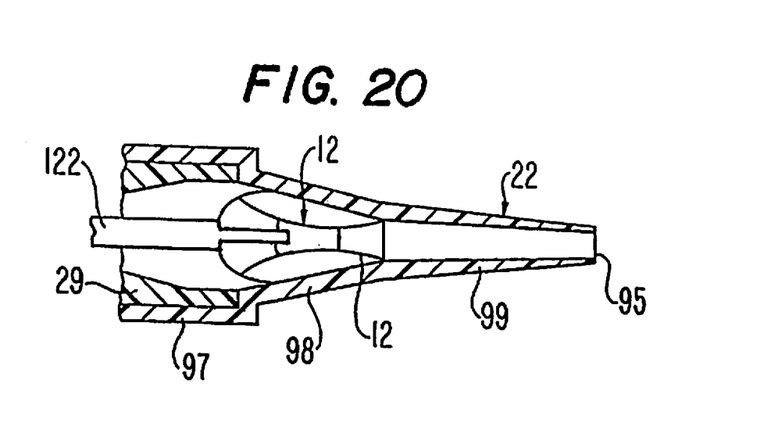

Once the lens has been inspected, the tubular unit can be assembled. A viscoelastic material, such as hyaluronic acid or hydroxypropyl methylcellulose is placed in the cannula 22, typically prior to attachment of the cannula 22 to the assembly, as a lubricant for the insertion process. Alternatively, other materials, such as balanced salt solution (BSS), could be also used. Once device 10 is assembled, the surgeon inserts the distal end of cannula 22 into the incision 142 in the eye 14. The surgeon then grasps lateral flanges 141 and pushes on pad 119 to move plunger 18 in a continuous forward motion. (FIG. 1). Due to this continuous movement of rod 122 through tubular unit 16, its distal end 128 engages lens 12 (FIG. 24). The proximal haptic 49a and possibly a portion of optic 48 are received into and held by slot 132, between walls 137a, 137b. The lens is then pushed forwardly by plunger 18 so that the distal side of optic 48 is shifted transversely toward cover 21 by sloped surfaces 59a, 59b of ramps 53a, 53b; that is, sloped surfaces 59a, 59b guide the central portion of optic 48 away from flats 52a, 52b (FIGS. 19 and 20). Inclined surface 88 and conical surface 91 provide ample clearance for this motion of the lens. As the center of the lens is shifted to move over ramps 53a, 53b, the sides of the lens are forced generally in the direction opposite to the ramps, by the inner wall surface 78 of cover 21. Specifically, the conical surface 91 in cover 21 causes lens 12 to curl downwardly and into troughs 75a, 75b. Continued advancement of lens 12 through the tapering passage of tubular unit 16 causes continued curling and compression of the lens.

The lens continues its forward motion until plunger 18 pushes lens 12 beyond cannula 22. In the preferred construction, plunger 18 is pushed manually forward in a controlled manner; although other means, such as a pneumatic drive may be used. The leading haptic 49b is fed into the distal cul-de-sac 152 of the capsular bag 154.

Figure 22:
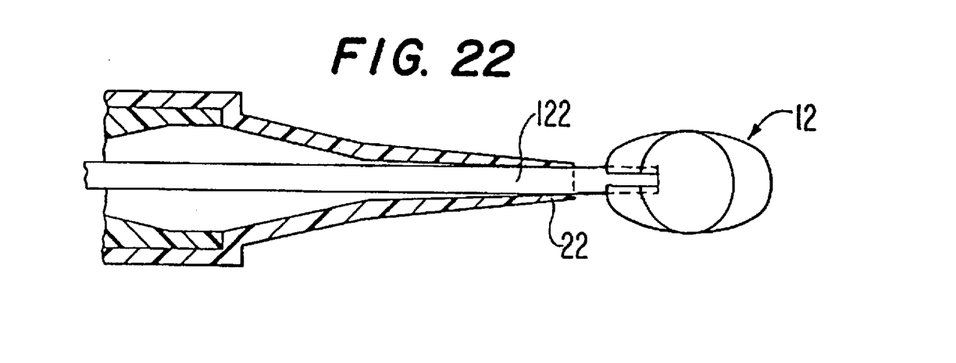
Figure 23:
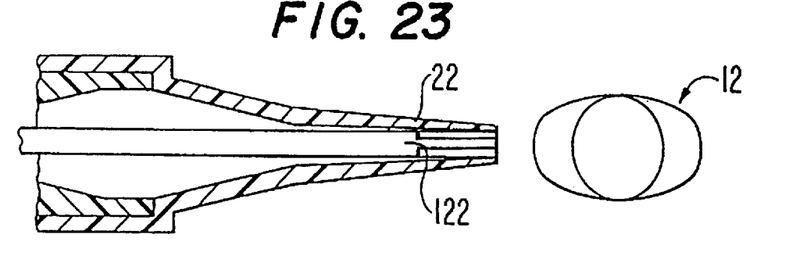

When lens 12 exits from cannula 22, it expands to its full unstressed state (FIGS. 22, 24 and 26). The lens, however, remains held in the slot 132 of plunger 18. In this way, the risk of the lens springing in an uncontrolled manner from the cannula and damaging the interior of the eye is alleviated. Holding the lens with the plunger also provides an increased control in placing the lens in the eye. To release the lens, the plunger is retracted into tubular unit 16 so that the lens is pushed from slot 132 by distal end 95 of cannula 22 (FIG. 23). The retraction of plunger 18 is preferably performed automatically by biased spring elements 140a, 140b when pressure is released from thumb pad 119. A further implement, or perhaps device 10 itself, will typically be required to properly position the proximal haptic 49a into capsular bag 154.

The above-discussion concerns the preferred embodiments of the present invention. Various other embodiments as well as many changes and alterations may be made without departing from the spirit and broader aspects of the invention as described in the claims. For example, although the preferred embodiments concern the insertion of a flexible IOL into the eye, the invention is not so limited. The teachings of the present invention are applicable to the insertion of flexible membranes generally, including synthetic membranes, biopolymer membranes, and natural body tissues.

We claim:

1. A device for inserting a flexible intraocular lens having an optic portion and a haptic portion into an eye, said device comprising:

a tubular member including a passage for receiving a lens, said passage having an open distal end for inserting the lens into an eye and a staging area for supporting the lens in a substantially unstressed state, said staging area including proximal and distal supporting surfaces for supporting the haptic portion of the lens so that the optic portion of the lens is suspended to substantially avoid contact of the optic portion with interior portions of said tubular member in said substantially unstressed state; and a plunger being movably received within said passage of said tubular member for moving the lens through said open distal end of said tubular member and into the eye.

2. A device in accordance with claim 1 in which said supporting surfaces include at least one distal support which is spaced from sidewalls of said passage to define gaps therebetween, wherein said distal support directs a central portion of the lens in one generally radial direction and said gaps receive side portions of the lens in an opposite generally radial direction as said lens is advanced by said plunger to direct folding of said lens in a predetermined direction.

3. A device in accordance with claim 1 in which said passage of said tubular member tapers as it extends from said staging area to said distal end.

4. A device in accordance with claim 1 in which said tubular member includes a cover which can be opened to expose the lens for inspection.

5. A device in accordance with claim 4 in which said tubular member further includes a separate cannula element which is received over said cover to hold said cover in a closed position.

6. A device in accordance with claim 1 in which said plunger includes a distal tip provided with means for holding the lens outside of said passage.

7. A device in accordance with claim 6 which further includes a spring element for retracting said distal tip of said plunger into said passage of said tubular member.

\* \* \* \* \*